(12) United States Patent
Thyagarajan

(10) Patent No.: US 11,141,585 B2
(45) Date of Patent: Oct. 12, 2021

(54) NON-INVASIVE NEURAL INTERFACE

(71) Applicant: Palo Alto Research Center Incorporated, Palo Alto, CA (US)

(72) Inventor: Krishnan Thyagarajan, Mountain View, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 284 days.

(21) Appl. No.: 16/235,634

(22) Filed: Dec. 28, 2018

(65) Prior Publication Data

US 2020/0206497 A1     Jul. 2, 2020

(51) Int. Cl.
| | |
|---|---|
| *A61N 1/32* | (2006.01) |
| *A61B 5/00* | (2006.01) |
| *A61N 1/40* | (2006.01) |
| *A61N 2/00* | (2006.01) |

(52) U.S. Cl.
CPC ............ *A61N 1/323* (2013.01); *A61B 5/4836* (2013.01); *A61B 5/6801* (2013.01); *A61B 5/6867* (2013.01); *A61N 1/40* (2013.01); *A61N 2/006* (2013.01)

(58) Field of Classification Search
CPC .......... A61N 1/323; A61N 1/40; A61N 2/006; A61B 5/4836; A61B 5/6801; A61B 5/6867; A61B 5/0476; A61B 5/01; A61B 5/02
USPC ........................................................ 607/115
See application file for complete search history.

(56) References Cited

U.S. PATENT DOCUMENTS

| | | | |
|---|---|---|---|
| 3,951,134 | A | 4/1976 | Malech |
| 5,284,144 | A | 2/1994 | Delannoy et al. |
| 6,646,533 | B2 | 11/2003 | Biegelson et al. |
| 2004/0230263 | A1 | 11/2004 | Samulski |
| 2008/0275289 | A1 | 11/2008 | Olree et al. |
| 2008/0284674 | A1 | 11/2008 | Herz et al. |

(Continued)

FOREIGN PATENT DOCUMENTS

| | | |
|---|---|---|
| CN | 102784436 | 11/2012 |
| EP | 2975693 | 1/2016 |

(Continued)

OTHER PUBLICATIONS

European Search Report from EP Application No. 19219898.4 dated Jun. 9, 2020, 7 pages.

(Continued)

*Primary Examiner* — Amanda K Hulbert
*Assistant Examiner* — Philip C Edwards
(74) *Attorney, Agent, or Firm* — Mueting Raasch Group

(57) ABSTRACT

A neuromodulator includes an electromagnetic (EM) wave generator configured to generate EM waves remote from a patient and to direct the EM waves to one or more target regions within the patient. Frequencies of the EM waves fall outside a range of frequencies that activates neurons. Intersection of the EM waves in each target region creates envelope-modulated electric and magnetic fields having one or more frequencies that fall within the range of frequencies that activates neurons. The neuromodulator includes control circuitry configured to control parameters of the EM waves produced by the EM wave generator. The neuromodulator may use feedback based on one or more of patient input and/or sensing of physiological signals in order to close the loop and control the EM waves.

20 Claims, 9 Drawing Sheets

(56) References Cited

U.S. PATENT DOCUMENTS

| | | |
|---|---|---|
| 2009/0018384 A1 | 1/2009 | Boyden et al. |
| 2010/0256438 A1* | 10/2010 | Mishelevich .......... A61N 2/006 600/13 |
| 2010/0028647 A1 | 11/2010 | Schneider et al. |
| 2010/0286470 A1 | 11/2010 | Schneider et al. |
| 2011/0199273 A1 | 8/2011 | Kim et al. |
| 2011/0213195 A1 | 9/2011 | Kraus et al. |
| 2011/0245900 A1 | 10/2011 | Turner et al. |
| 2012/0065714 A1 | 3/2012 | Szasz et al. |
| 2012/0101327 A1 | 4/2012 | Dissing et al. |
| 2012/0229339 A1 | 9/2012 | Higgins |
| 2013/0096363 A1 | 4/2013 | Schneider et al. |
| 2014/0257438 A1 | 9/2014 | Simon et al. |
| 2014/0357935 A1 | 12/2014 | Ilmoniemi et al. |
| 2015/0080637 A1 | 3/2015 | Bonmassar et al. |
| 2015/0283395 A1 | 10/2015 | Sabouni |
| 2015/0328477 A1 | 11/2015 | Gale et al. |
| 2016/0023016 A1 | 1/2016 | Bonmassar et al. |
| 2016/0166843 A1 | 6/2016 | Casse et al. |
| 2016/0220838 A1 | 8/2016 | Scheinowitz et al. |
| 2017/0014637 A1 | 1/2017 | Basser |
| 2017/0120041 A1* | 5/2017 | Wenger .............. A61N 1/36002 |
| 2017/0216594 A1* | 8/2017 | Grossman .......... A61N 1/36146 |
| 2017/0225004 A1 | 8/2017 | Casse et al. |
| 2017/0246481 A1 | 8/2017 | Mishelevich |

FOREIGN PATENT DOCUMENTS

| | | |
|---|---|---|
| EP | 2975694 | 1/2016 |
| EP | 2288409 | 10/2018 |
| WO | 2004/064915 | 8/2004 |
| WO | 2004/082759 | 9/2004 |

OTHER PUBLICATIONS

Bonmassar et al., "Optimizing Microscopic Magnetic Fields for Neuronal Stimulation", International Journal of Bioelectromagnetism, vol. 16, No. 1, 2014, pp. 1-31.

Dmochowski et al., "Noninvasive Neuromodulation Goes Deep", Cell, 169 (6), Jun. 2017, pp. 977-978.

Ge et al., "A Design of Array Transcranial Magnetic Stimulation Coil System", International Science Index, Biomedical and Biological Engineering, vol. 6, No. 5, 2012, 4 pages.

Goats, :Interferential Current Therapy, Br. J. Sp. Med, vol. 24, No. 2, Jun. 1, 1990, pp. 87-92.

Grossman et al., "Noninvasive Deep Brain Stimulation via Temporally Interfering Electric Fields", Cell, 169, Jun. 1, 2017, pp. 1029-1041.

Rohde et al., "Focused High Frequency Repetitive Transcranial Magnetic Stimulation for Localisation of the Unexposed Primary Motor Cortex During Brain Tumour Surgery", Journal of Neurology, Neurosurgery & Psychiatry, 2003; 74, 1283-1287.

* cited by examiner

NON-INVASIVE NEURAL INTERFACE

BACKGROUND

Neuromodulation involves stimulating nerves to alter nerve activity and is one of the most exciting emerging therapies for treatment of a broad range of diseases and conditions. For example, neuromodulation has the potential to provide important and life changing therapy for intractable pain, spinal cord injuries, headaches, Parkinson's disease, Alzheimer's disease, depression, and many other afflictions.

SUMMARY

Some embodiments are directed to a system that includes a neuromodulator. The neuromodulator includes an electromagnetic (EM) wave generator configured to generate EM waves remote from a patient and to direct the EM waves to one or more target regions within the patient. Frequencies of the EM waves fall outside a range of frequencies that activates neurons. Intersection of the EM waves in each target region creates envelope-modulated electric and magnetic fields having one or more frequencies that fall within the range of frequencies that activates neurons. The neuromodulator includes control circuitry configured to control parameters of the EM waves produced by the EM wave generator.

According to some aspects, the system further includes a receiver configured to receive EM waves from the target region wherein the received EM waves are modulated by neural activity signals within the target region.

Some embodiments involve a process that includes generating electromagnetic (EM) waves at a location remote from a patient, wherein frequencies of the EM waves fall outside a range of frequencies that activate neurons. The EM waves are directed to one or more target region within the patient where they intersect. In each target region, intersection of the EM waves creates envelope-modulated electrical and magnetic fields having frequencies falling within the range of frequencies that activates neurons. The characteristics of the envelope-modulated electrical and magnetic fields can be altered by changing the parameters of the intersecting EM waves. The process may further include receiving EM waves modulated by a neural activity signal generated by neural activity within the target region.

BRIEF DESCRIPTION OF THE DRAWINGS

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

With an increasing trend of various forms of mental affliction among humans in present society, being able to sense and address parts of the brain on demand—either to sense or stimulate or stimulate and simultaneously sense neural activity has important therapeutic consequences. Approaches discussed herein involve temporal interference phased-array stimulation and/or sensing (TIPS) that takes advantage of temporal interference between two electromagnetic (EM) waves to provide localized steerable neural interaction. Apart from a huge potential in treating and understanding mental illnesses, the approaches discussed herein provide an invaluable tool for researchers in neuroscience.

The neuromodulation devices disclosed herein can provide minimally-invasive and/or feedback-controlled neuromodulation and/or neural sensing within the brain and/or for peripheral nerves such as the vagus nerve or various other neural tissue in the body. The ability to selectively sense and/or stimulate nerve fascicles within a relatively small region enables treatment of a wide-range of peripheral and central nervous system disorders with targeted therapies.

Figure 1:
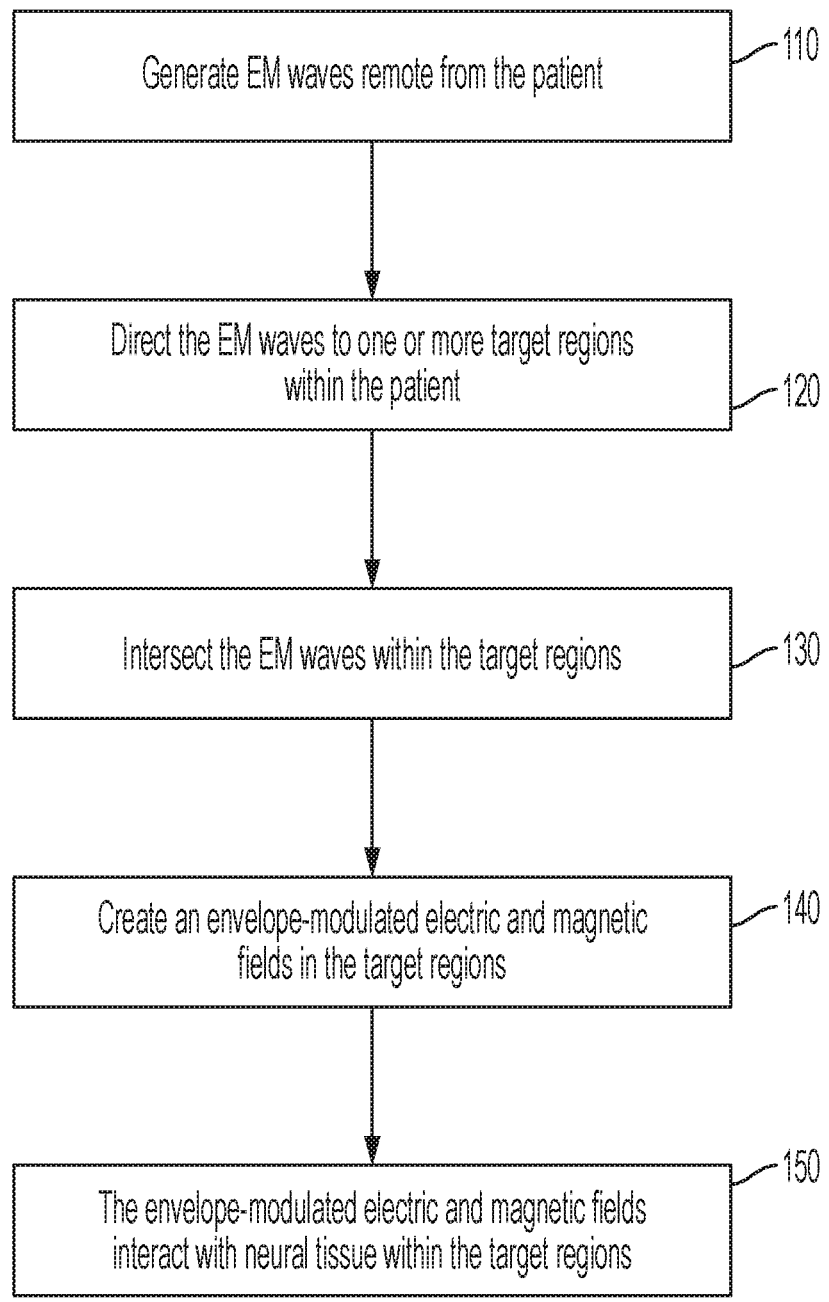
FIG. 1 is a flow diagram illustrating a neuromodulation process in accordance with some embodiments.

Turning now to FIG. 1 there is shown a flow diagram that illustrates a neuromodulation process in accordance with some embodiments. Electromagnetic (EM) waves are generated 110 at one or more locations remote from the patient. For example, the remote locations may be spaced apart from the patient by a few centimeters, a meter, or more than a meter such that the source of the EM waves does not come into contact the patient. The EM waves have frequencies that exceed the range of frequencies capable of causing activation of neurons, e.g., frequencies greater than about 100 kHz. The EM waves are directed 120 to one or more target regions within the body of the patient where the EM waves intersect 130 with one another. In each target region, the intersecting EM waves create 140 envelope-modulated electric and magnetic fields that interact 150 with the neural tissue and neurons within the target region. In some implementations, therapeutic neurostimulation can be provided by electric and/or magnetic fields that provide stimulation above the threshold required for activation of neurons. In some implementations, therapeutic neurostimulation can be by electric and/or magnetic fields that are below the threshold required for activation of the neurons. In some embodiments, the magnitude and/or degree of modulation of the envelope-modulated fields stimulate the neurons in the target region causing them to fire. In other embodiments, the magnitude and/or degree of modulation of the envelope-modulated fields are below the threshold required for activation of the neurons in the target region.

Figure 2:
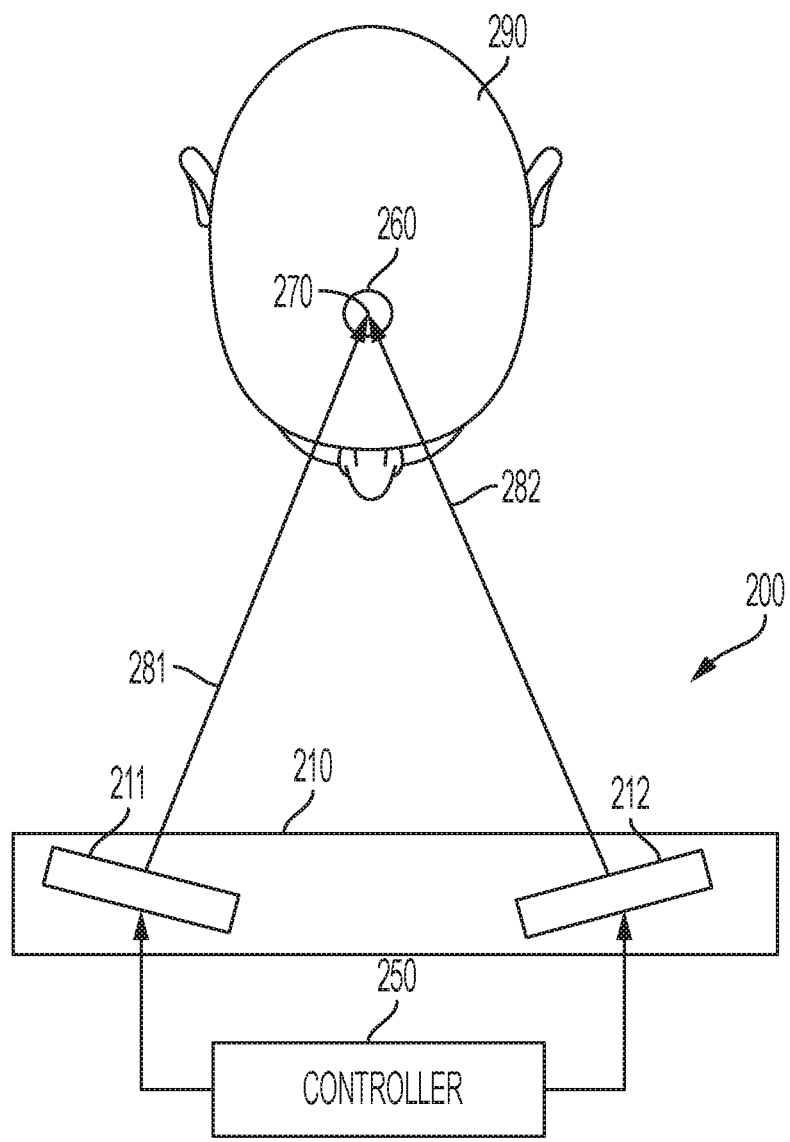
FIG. 2 is a block diagram of a neuromodulator in accordance with some embodiments.

FIG. 2 is a block diagram of a neuromodulator 200 in accordance with some embodiments. The neuromodulator 200 includes an EM wave generator 210 that generates and transmits multiple EM waves. For example, as shown in FIG. 2, the EM wave generator 210 may generate first and second signals that are transmitted by components 211, 212 as first and second EM waves 281, 282. The EM waves 281, 282 are directed to one or more target regions 260 within the body 290 of a patient. In FIG. 2, the target region 260 is shown within the patient's brain, however, it will be appreciated that target regions may be located within other parts of the patient's body.

The EM waves 281, 282 intersect within the target region 260. Linear superposition of the EM waves 281, 282 in the target region 260 causes a temporal variation in the electric and magnetic fields 270 in the target region 260 that differs from the temporal variation of the incident EM waves 281, 282. The linear superposition of the waves 281, 282 creates envelope-modulated electric and magnetic fields 270 in the target region 260. Modulation of the envelope occurs at a frequency which is a difference between the frequencies of the incident EM waves. The first EM wave 281 may be expressed mathematically as $A_1 \sin w_1(x)$, where $A_1$ represents the amplitude of the first EM wave 281 and $w_1$ represents the frequency of the EM wave 281. The second EM wave 282 may be expressed mathematically as $A_2 \sin(1+\alpha)w_1(x)$, where $A_2$ represents the amplitude of the second EM wave 282 and $(1+\alpha)w_1$ represents the frequency of the second EM wave 282. In the target region 260, the first and second EM waves combine to form envelope-modulated fields which can be expressed as $A_1 \sin w_1(x)+A_2 \sin(1+\alpha)w_1(x)$. Note that $\alpha$ could be negative.

Figure 3A:
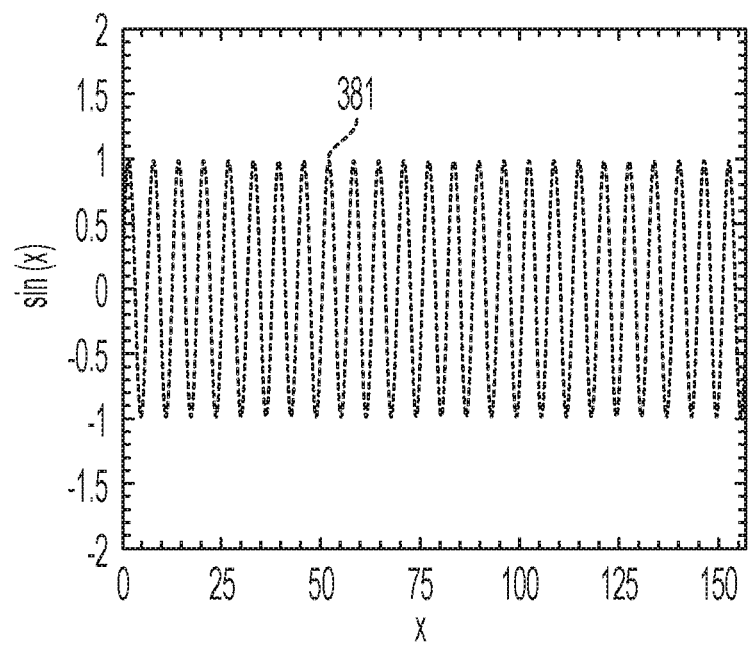
FIG. 3A provides a graph of a first EM wave having the form sin (x)
Figure 3B:
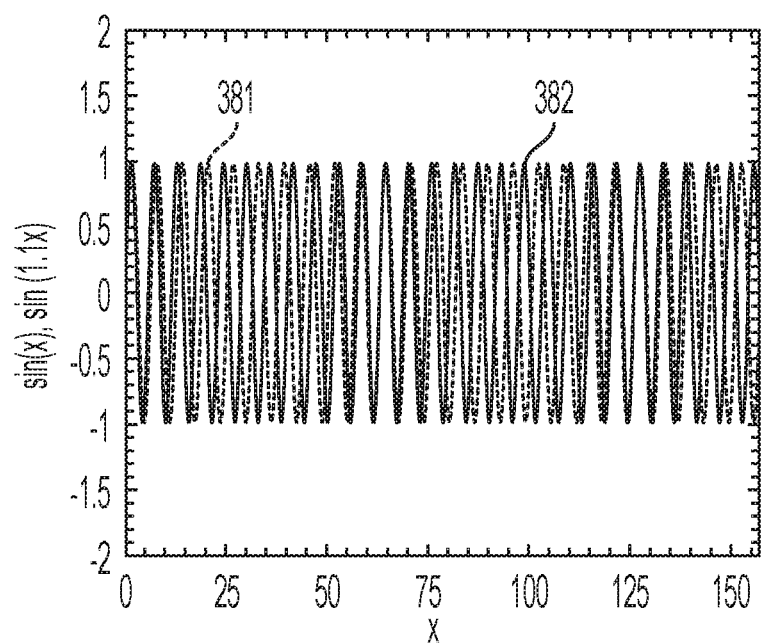
FIG. 3B provides a graph of a second EM wave having the form sin (x+0.1x), superimposed on the first EM wave of FIG. 3A.
Figure 3C:
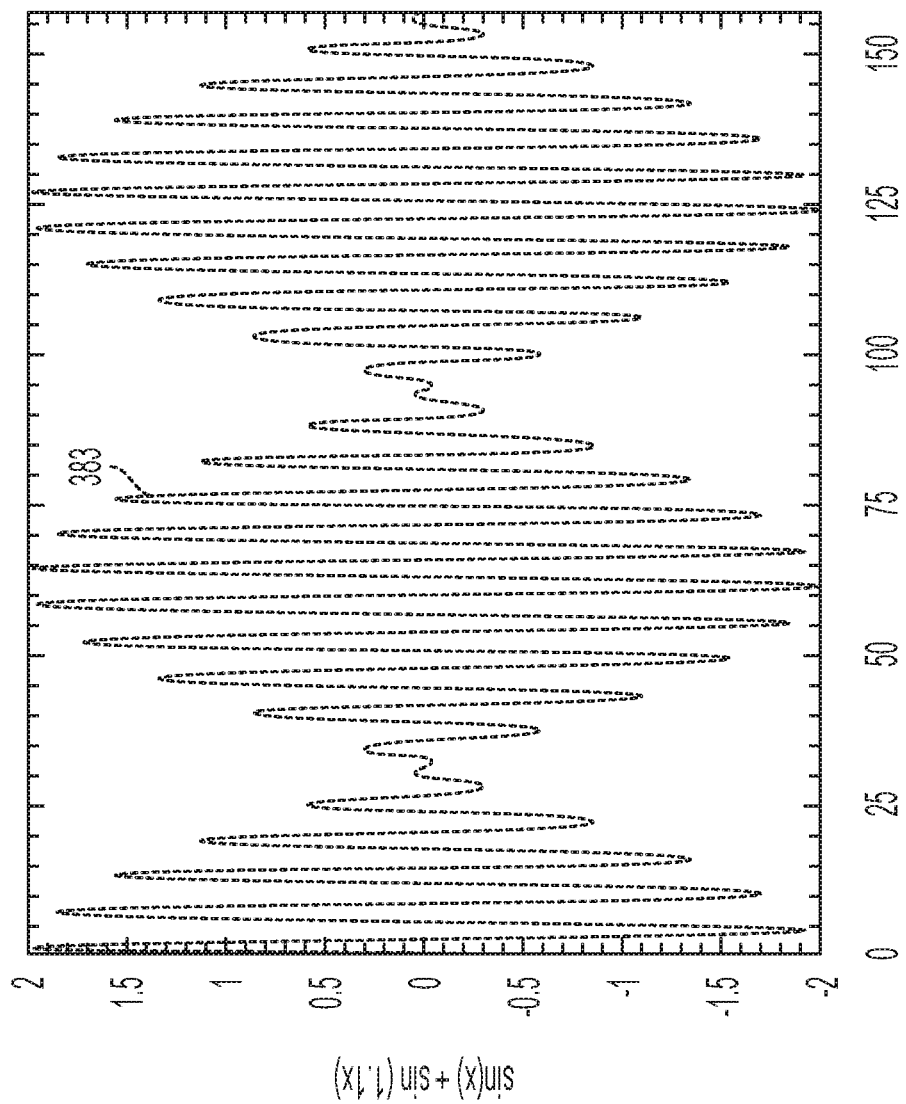
FIG. 3C depicts the combination of the first and second EM waves of FIGS. 3A and 3B, the combination forming envelope-modulated fields having the form sin (x)+sin(x+0.1x) in accordance with some embodiments.

For example, FIG. 3A provides a graph of a first EM wave 381, $\sin(x)$, and FIG. 3B provides a graph of a second EM wave 382, $\sin(x+0.1x)$, superimposed on the first EM wave 381. As depicted in FIG. 3C, the first and second EM waves 381, 382 combine to form envelope-modulated fields 383, $\sin(x)+\sin(x+0.1x)$ in this example.

Returning to FIG. 2, the neuromodulator 200 includes a controller 250 that can control parameters of the EM waves 281, 282, such as frequency, phase, and/or amplitude. Changing the parameters of the EM waves 281, 282 can be used to modify one or more characteristics of the envelope-modulated fields 270 in the target regions 260. For example, the controller 250 may change one or more of frequency, amplitude, and modulation depth of the envelope-modulated fields 270 by modifying the frequency, phase, and/or amplitude of the EM waves 281, 282.

Each target region 260 may have volume of less than about 5 cm×5 cm×5 cm, or less than 125 cm$^3$) or even less than about 30 cm$^3$, or 2 cm×2 cm×2 cm, or less than about 8 cm$^3$. In some embodiments, the controller 250 may control the parameters of the first and second EM waves 281, 282 such that a maximum amplitude of the envelope-modulated fields 270 fall within the target region 260. In some embodiments, the controller 250 may control the parameters of the first and second EM waves 281, 282 such that a maximum degree of modulation of the envelope-modulated fields 270 fall within the target region 260.

In some embodiments the EM waves 281, 282 that intersect within the target regions 260 are composites of multiple EM waves generated by the EM wave generator 210 of the neuromodulator 200. The neuromodulator 200 may comprise phased array that produces multiple EM waves that undergo constructive and/or destructive interference as they travel toward the patient. The controller 250 controls the parameters of the multiple EM waves, e.g., frequency, phase, and/or amplitude, generated by the phased array to beam steer and/or focus the intersecting EM waves to at least one target region 260.

In some implementations, the frequencies of the first and second EM waves 281, 282 may operate within FDA-approved WiFi bands, such as the 2.45 GHz frequency. These FDA-approved bands have been the subject of extensive research showing that these frequencies do not cause adverse reactions in people. In some embodiments, the frequencies of the EM waves 281, 282 may be greater than about 1 MHz and the frequencies of the envelope-modulated electric and magnetic fields are less than about 100 kHz. In some embodiments, the frequencies of the EM waves may be greater than about 150 kHz and frequencies of the envelope-modulated electric and magnetic fields are less than about 100 kHz.

Figure 4:
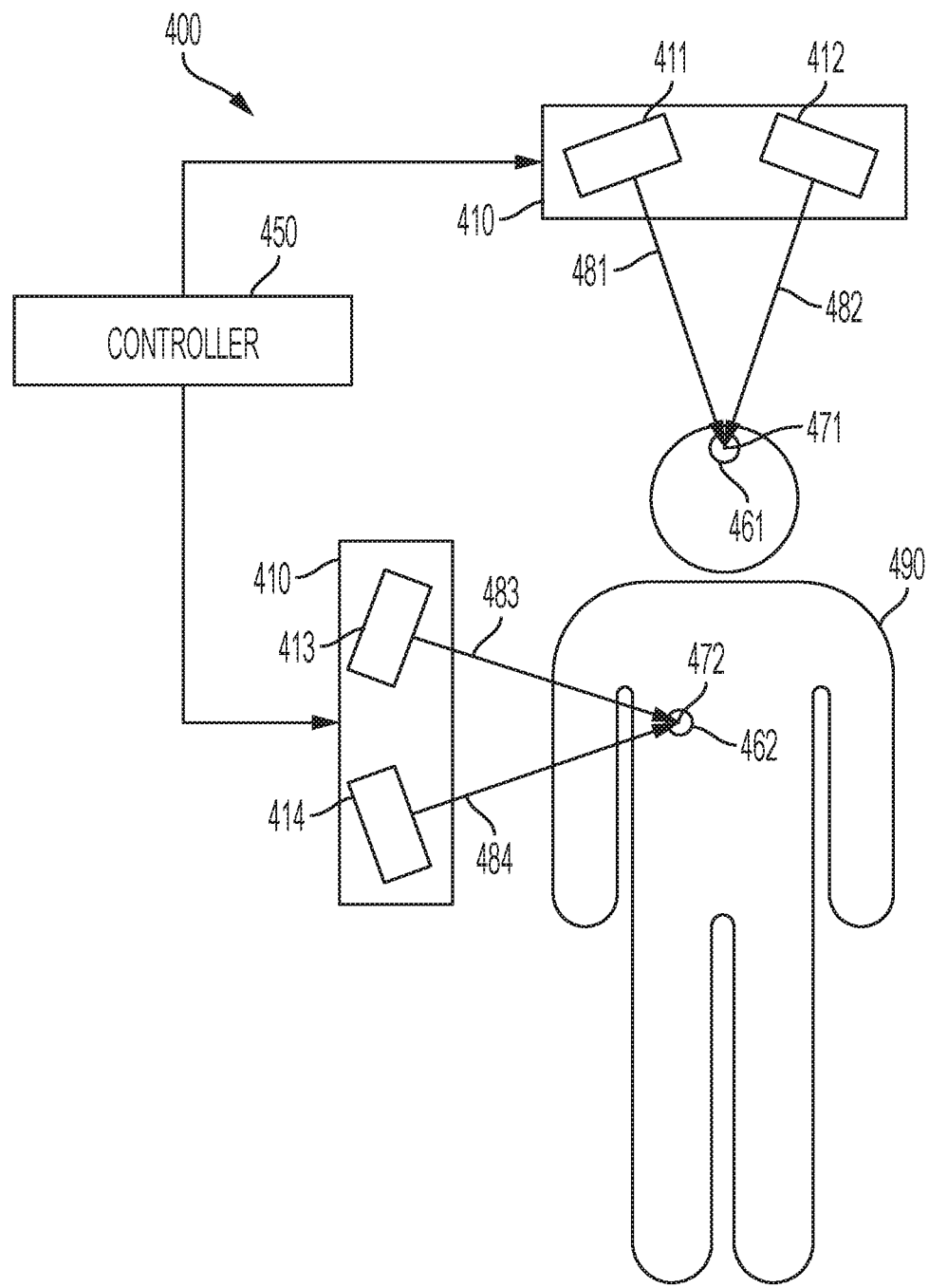
FIG. 4 depicts another example of a neuromodulator comprising multiple target regions in accordance with some embodiments.

FIG. 4 depicts another example of a neuromodulator 400 in accordance with some embodiments. Neuromodulator 400 includes an EM generator 410 capable of generating EM waves 481, 482, 483, 484 that intersect at multiple target regions 461, 462 within the patient's body 490. As depicted in FIG. 4, the target regions 461, 462 may be in the patient's brain or at other locations. EM waves 481, 482 intersect in target region 461.

The first EM wave 481 may be expressed mathematically as $A_1 \sin w_1(x)$, where $A_1$ represents the amplitude of the first EM wave 481 and $w_1$ represents the frequency of the EM wave 481. The second EM wave 482 may be expressed mathematically as $A_2 \sin(1+\alpha)w_1(x)$, where $A_2$ represents the amplitude of the second EM wave 482 and $(1+\alpha)w_1$ represents the frequency of the second EM wave 482. In the target region 461, the first and second EM waves 481, 482 combine to form envelope-modulated fields 471 which can be expressed as $A_1 \sin w_1(x)+A_2 \sin(1+\alpha)w_1(x)$.

The third EM wave 483 may be expressed mathematically as $B_1 \sin w_2(x)$, where $B_1$ represents the amplitude of the second EM wave 483 and $w_2$ represents the frequency of the EM wave 483. The fourth EM wave 484 may be expressed mathematically as $B_2 \sin(1+\beta)w_2(x)$, where $B_2$ represents the amplitude of the second EM wave 484 and $(1+\beta)w_2$ represents the frequency of the fourth EM wave 484. In the target region 462, the third and fourth EM waves 483, 484 combine to form envelope-modulated fields 472 which can be expressed as $B_1 \sin w_2(x)+B_2 \sin(1+\beta)w_2(x)$.

As previously discussed, the controller 450 may control one or more parameters of one or more of the first, second, third, and fourth EM waves 481-484 to control characteristics of the envelope-modulated fields 471, 472 respectively created in the target regions 461, 462. Additionally or alternatively, using a phased array and the technique of constructive and destructive interference, the controller 450 may control one of more parameters of multiple EM waves generated by the neuromodulator to beam steer and/or focus the composite EM waves 481-484 to the target regions 461, 462

Figure 5:
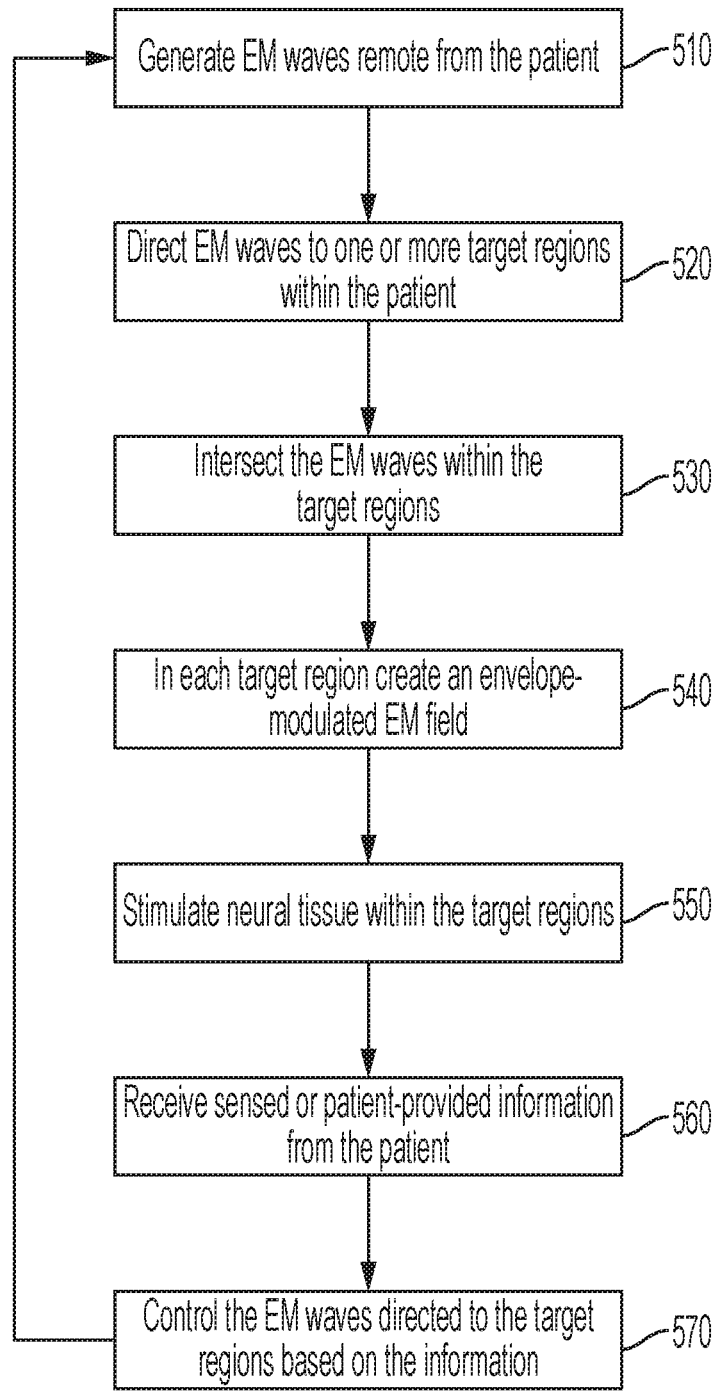
FIG. 5 is a flow diagram illustrating a process of providing neuromodulation with feedback in accordance with some embodiments.

In some embodiments, the parameters of the intersecting EM waves can be altered by the controller based on patient information provided to the controller. FIG. 5 is a flow diagram illustrating a process of providing neuromodulation with feedback. According to these processes EM waves are generated 510 at one or more locations remote from the patient wherein the source of the EM waves does not come into contact the patient. The EM waves have frequencies that exceed the range of frequencies capable of causing activation of neurons. The EM waves are directed 520 to one or more target regions within the body of the patient where the EM waves intersect 530 with one another. In each target region, the intersecting EM waves create 540 envelope-modulated electric and magnetic fields that interact 550 with the neural tissue within the target region. The controller may include communications circuitry that allows the controller to receive 560 patient information from a device configured to gather information about the patient. The patient information may be obtained by sensors attached to the patient or implanted within the patient, for example. The patient information may alternatively or additionally be gathered by a device that provides a user interface allowing the patient or another operator to enter information. The controller controls parameters 570 of the intersecting EM waves to alter characteristics of the envelope-modulated fields within the target regions based on the patient information. The patient information may also be obtained by analyzing the signal reflected back, in order to determine the overlaying modification that has been caused to the original impinging radiation.

Figure 6:
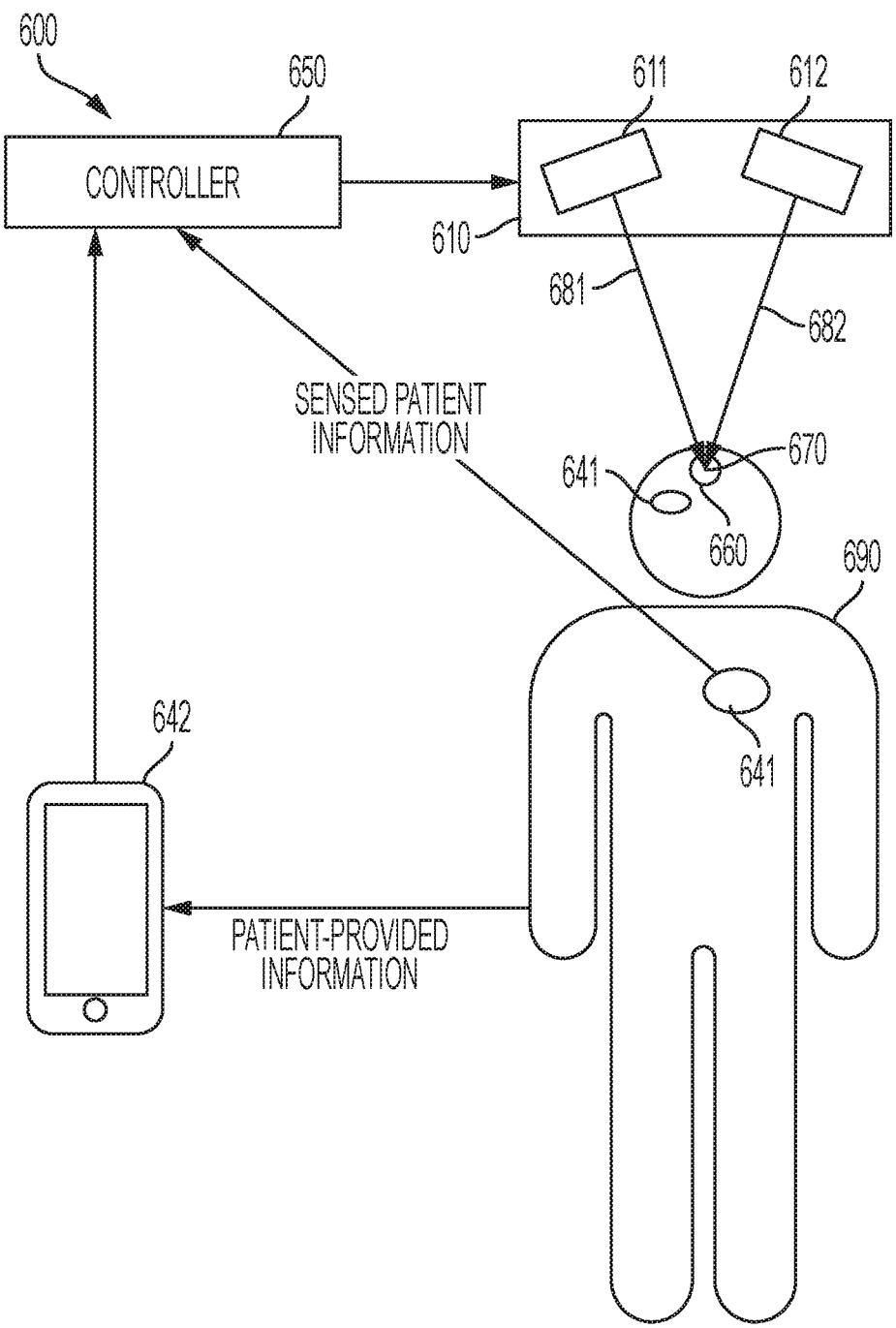
FIG. 6 is a block diagram of a neuromodulator that includes one or more devices for obtaining patient information in accordance with some embodiments.

FIG. 6 is a block diagram of a neuromodulator 600 in accordance with some embodiments. The neuromodulator 601 includes an EM wave generator 610 that generates and transmits multiple EM waves. For example, as shown in FIG. 6, the EM wave generator 610 may generate first and second signals that are transmitted by components 611, 612 as first and second EM waves 681, 682. The EM waves 681, 682 are directed to one or more target regions 660 within the body 690 of a patient. In FIG. 6, the target region 660 is shown within the patient's brain, however, it will be appreciated that target regions may be located within other parts of the patient's body.

The EM waves 681, 682 intersect within the target region 660. Linear superposition of the EM waves 681, 682 in the target region 660 causes a temporal variation in the electric and magnetic fields in the target region 660 that differs from the temporal variation of the incident EM waves 681, 682. The linear superposition of the waves 681, 682 creates envelope-modulated electric and magnetic fields 670 in the target region 660. Modulation of the envelope occurs at a frequency which is a difference between the frequencies of the incident EM waves 681, 682.

The neuromodulator 600 includes a controller 650 that can control parameters of the EM waves 681, 682, such as frequency, phase, and/or amplitude. Changing the parameters of the EM waves 681, 682 can be used to modify one or more characteristics of the envelope-modulated fields 670 in the target regions 660.

The controller 650 may be programmed to control the characteristics of the envelope-modulated fields 670 to provide a prescribed therapy or to achieve (or approach) a specific patent condition. For example, the controller 650 may change one or more of frequency, amplitude, and modulation depth of the envelope-modulated fields 670 by modifying the frequency, phase, and/or amplitude of the EM waves 681, 682.

According to some embodiments, the patient information device 641 comprises one or more sensors. FIG. 6 shows two possible locations for the patient information device 641—one proximate to the site of the stimulation and one farther from the stimulation site. In general, there may be one or multiple patient information devices located within, on, or around the patient. The patient information devices may communicate directly with the controller 650 or may communicate with another device, such as a hand-held device. The patient information device 641 provides sensed patient information to the controller 650 which modifies the EM waves 681, 682 based on the sensed patient information. For example, one or more sensors may be attached to the patient 690, implanted within the patient 690, or otherwise disposed to sense patient information. The patient information device 641 may be coupled to the controller 650 through a wired or wireless communications link, for example. According to some implementations, the patient information device 641 may be incorporated within an implantable diagnostic or therapeutic device, such as a cardiac pacemaker, that wirelessly communicates with the neuromodulation controller 650. In some embodiments, the patient information device 641 measures biological signals such as heart rate (HR), blood pressure (BP), respiratory rate (RR), body temperature, etc., non-invasively.

According to some embodiments, patient information may be obtained from a device 642 that provides a user interface which allows the patient or another operator to enter the patient information and/or record the patient response to a series of questions. The patient information entered may include measured values, e.g., heart rate, respiration rate, temperature, and/or may include subjective information, such as mood, perceived pain level, and/or other perceptions of psychological state, tracking and responding to certain visual or auditory stimuli in the field of view of the user.

One or both patient information devices 641, 642 may be configured to monitor dynamically changing physiological patient information, e.g., heart rate, respiration rate, blood pressure, body temperature, etc., and to communicate the patent information to the controller 650. In response, the controller 650 alters one or more parameters of the EM waves 681, 682 that create the envelope-modulated fields 670 within the target region 660. Components of the neuromodulator 600, e.g., the controller 650 and/or the patient information devices 641, 642 may synthesize and analyze both stimulation and sensing data by utilizing self-learning algorithms, and may be configured to adapt the EM waves 641, 642 in real-time to enhance therapeutic efficacy.

Based on the patient information obtained from devices 641, 642, the controller may develop a dynamic profile of biological conditions that occur in response to stimulation of the nerves within the target region 660. Optimal profiles of biological conditions that provide accurate feedback control for the neuromodulation function may be developed for each target region 660.

The approaches described with reference to FIGS. 1-6 illustrate a "write-in" capability of the neuromodulator that can be used to provide neural stimulation to the patient. For example, the neuromodulator can be configured to create envelope-modulated electric and magnetic fields in target regions of a patient's body that provide a prescribed neuromodulation therapy to the target regions. In some embodiments, the envelope-modulated fields may have a field strength sufficient to activate neurons in the target regions causing them to fire. In some embodiments, the field strength of the envelope modulated fields may be below the threshold to activate the neurons, providing a sub-threshold therapy which sensitizes the neurons for activation but does not cause activation. In some implementations, the approach described above may be used with an existing technology such as superconducting quantum interference devices (SQUID) magnetoencephalography (MEG), in which different target regions of the brain are activated using the neuromodulator described above while the SQUID MEG maps out magnetic fields from the brain.

In addition to the "write-in" capability of the neuromodulator, a system may have "read-out" capability that allows monitoring of the neural activity within the target region. The neural activity within a target region can be read out when the neural activity within the target region modulates the envelope-modulated fields (also referred to as the interference signal) created by superposition of the EM waves in the target region. The modulation of the interference signal by neural activity results in EM waves that deviate from EM waves that are expected in the absence of neural activity. The EM waves are received at a receiver and the modulation caused by neural activity extracted from the received EM waves.

Figure 7:
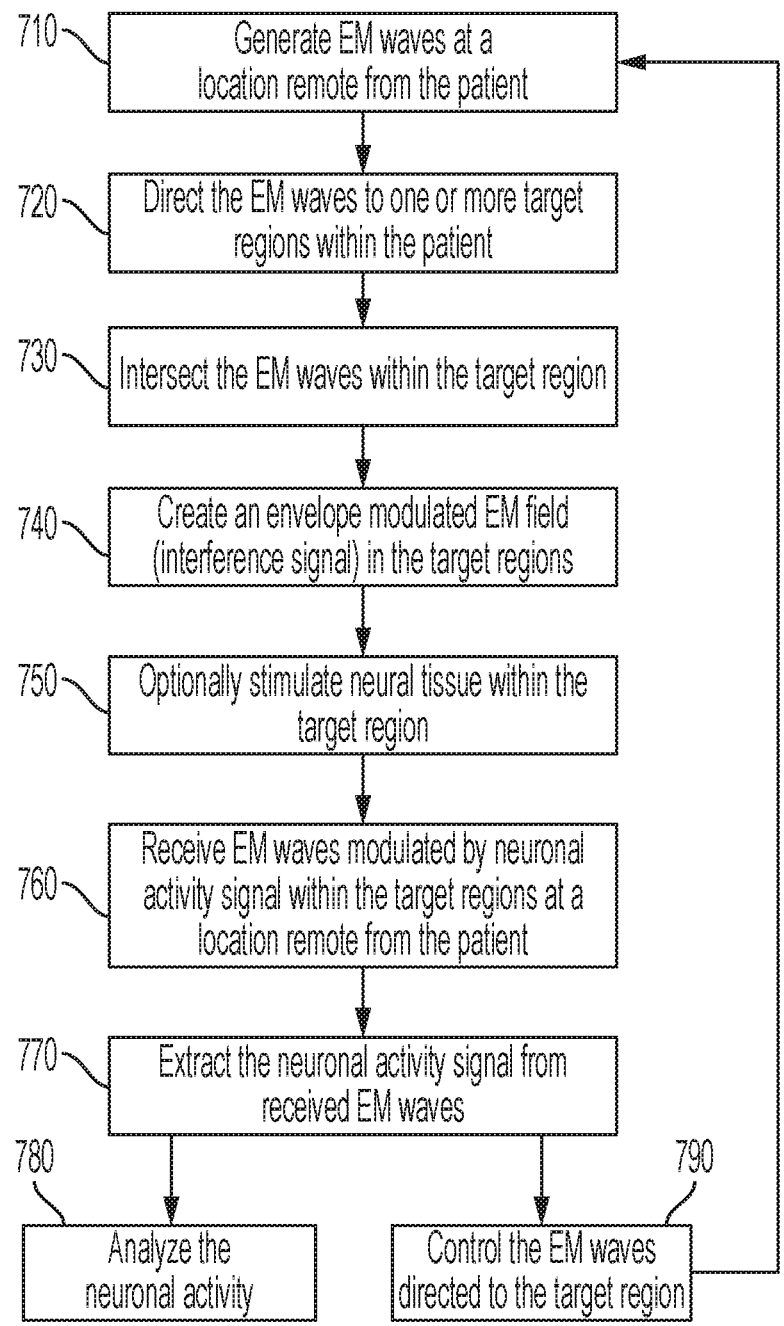
FIG. 7 is a flow diagram of a process that includes detecting neural activity in one or more target regions in accordance with some embodiments.

FIG. 7 is a flow diagram of a process that includes detecting neural activity in one or more target regions in accordance with some embodiments. Electromagnetic waves are generated 710 at one or more locations remote from the patient wherein the source of the EM waves does not come into contact the patient. The EM waves have frequencies that exceed the range of frequencies capable of causing activation of neurons. The EM waves are directed 720 to one or more target regions within the body of the patient where the EM waves intersect 730 with one another. In each target region, the intersecting EM waves create 740 an interference signal comprising envelope-modulated electric and magnetic fields. Optionally in some embodiments, the interference signal is configured to stimulate 750 the neurons within the target region.

The interference signal is modulated by a neural activity signal generated by neural activity within the target region. The modulated interference signal is transmitted from the target region as a neural-activity-modulated EM wave. The neural-activity-modulated EM wave is received 760 by a receiver. Optionally the neural activity signal can be extracted 770 from the neural-activity-modulated EM wave and analyzed 780 to obtain information about the neural activity. Optionally, the neural activity signal can be used to control 790 neural stimulation at the target region and/or can be used to control other therapies and/or processes.

Figure 8:
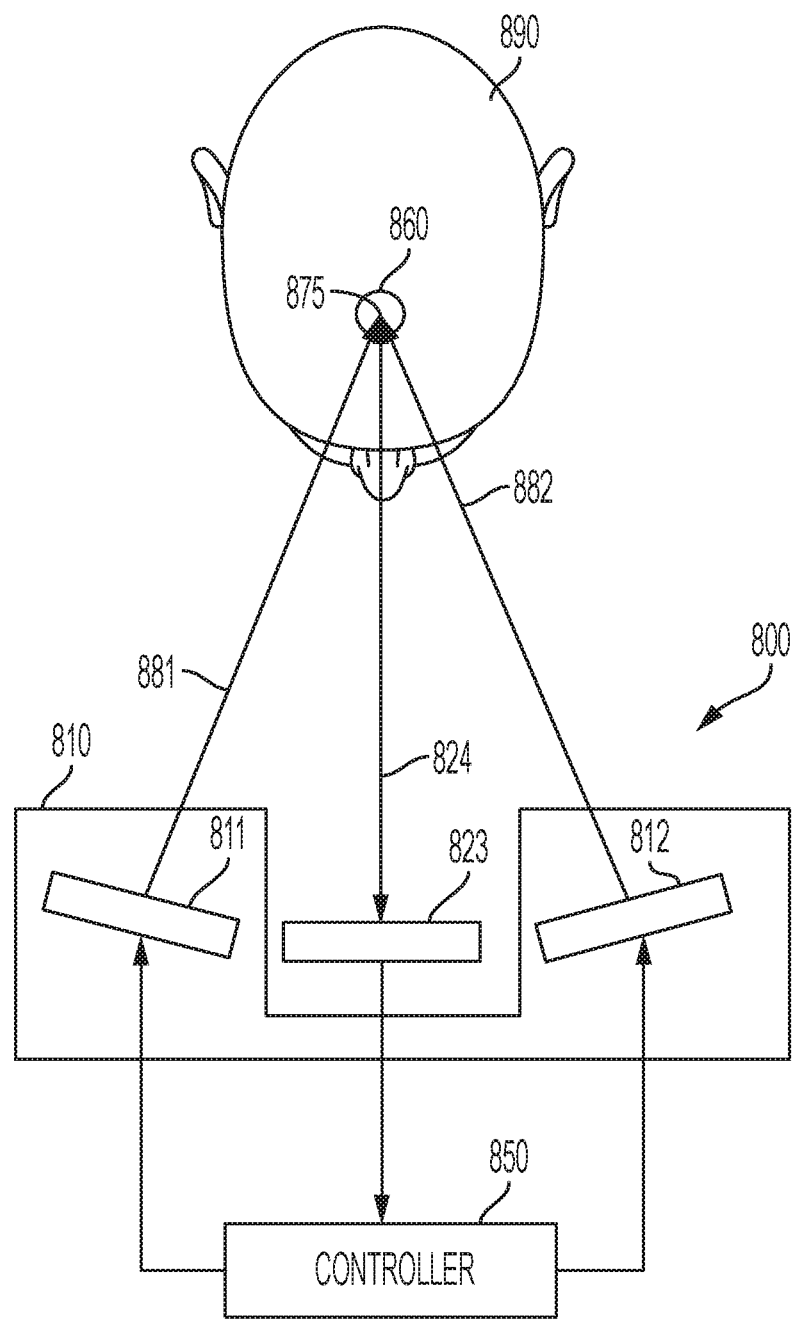
FIG. 8 is a block diagram of a system that is capable or stimulating neural activity and sensing neural activity in one or more target regions within a patient in accordance with some embodiments.

FIG. 8 is a block diagram of a system 800 that is capable or stimulating neural activity and sensing neural activity in one or more target regions 860 within a patient 890 in accordance with some embodiments. The system 800 includes an EM wave generator 810 that generates and transmits multiple EM waves. For example, as shown in FIG. 8, the EM wave generator 810 may generate first and second signals that are transmitted by components 811, 812 as first and second EM waves 881, 882. The EM waves 881, 882 are directed to one or more target regions 860 within the body 890 of a patient. In FIG. 8, the target region 860 is shown within the patient's brain, however, it will be appreciated that target regions may be located within other parts of the patient's body.

The EM waves 881, 882 intersect within the target region 860. Linear superposition of the EM waves 881, 882 in the target region 860 causes a temporal variation in the electric and magnetic fields 870 in the target region 260 that differs from the temporal variation of the incident EM waves 881, 882. The linear superposition of the waves 881, 882 creates envelope-modulated electric and magnetic fields, also referred to as the interference signal in the target region 860. Modulation of the interference signal occurs at a frequency which is a difference between the frequencies of the incident EM waves 881, 882.

The interference signal may be further modulated by a neural activity signal generated by neural activity in the target region. The neural activity may be stimulated by the interference signal, for example. The modulated interference signal is transmitted from the target region 860 as a neural-activity-modulated EM wave 824. The system 800 includes a receiver 823 configured to receive the neural-activity-modulated EM wave 824.

The system 800 includes a controller 850 coupled to the EM wave generator 811 and the receiver 823. The controller 850 can be configured to demodulate the received neural-activity-modulated EM wave 824 to extract the neural activity signal from the neural-activity-modulated EM wave 824. The controller 850 can be configured to control parameters of the EM waves 881, 882, such as frequency, phase, and/or amplitude. Changing the parameters of the EM waves 281, 882 can be used to modify one or more characteristics of the interference signal in the target regions 860. For example, the controller 850 may change one or more of frequency, amplitude, and modulation depth of the interference signal by modifying the frequency, phase, and/or amplitude of the EM waves 881, 882. In some implementations, the controller 850 may change the parameters of the EM waves 881, 882 based on the neural activity signal extracted from the neural-activity-modulated EM wave 824. For example, the controller 850 may change the characteristics of the interference signal, e.g., the amplitude and/or degree of modulation until the neural activity signal extracted from the neural-activity-modulated EM wave 824 indicates that a desired level of neural activity is being produced by the interference signal.

Although FIG. 8 depicts the same target region being stimulated and sensed, it is also possible for one or more first target regions to be neurally stimulated by the neuromodulator portion of the system and neural activity sensed from one or more second target regions. The system may be configured to write in neural stimulation and read out neural activity from multiple target regions within the body. The system may be configured to write-in neural stimulation at one or more first locations and read out neural activity from one or more second locations. For example, consider a system capable of addressing multiple target regions within the body. The system may simultaneously write in neural stimulation to each of the multiple target regions. The system may sequentially write in neural stimulation to each of the multiple target regions or may sequentially write in neural stimulation to one or more groups of the multiple target regions. Similarly, the system may simultaneously read out neural activity from each of the multiple target regions. The system may sequentially read out neural activity from each of the multiple target regions or may sequentially read out neural activity from one or more groups of the multiple target regions. In some implementations, the system may write in neural stimulation to one or more first target regions and may read out neural activity from one or more second target regions.

The foregoing description of various embodiments has been presented for the purposes of illustration and description and not limitation. The embodiments disclosed are not intended to be exhaustive or to limit the possible implementations to the embodiments disclosed. Many modifications and variations are possible in light of the above teaching.

The invention claimed is:

1. A system, comprising:
   a neuromodulator comprising:
      an electromagnetic (EM) wave generator configured to generate EM waves remote from a patient and to direct the EM waves to one or more target regions within the patient, frequencies of the EM waves falling outside a range of frequencies that activates neurons, intersection of the EM waves in each target region creating envelope-modulated electric and magnetic fields having one or more frequencies that fall within the range of frequencies that activates neurons; and control circuitry configured to control one or more parameters of the EM waves produced by the EM wave generator;

wherein the frequencies of the EM waves are greater than about 150 kHz and frequencies of the envelope-modulated electric and magnetic fields are less than about 100 kHz.

2. The system of claim 1, wherein the control circuitry is configured to control the one or more parameters of the EM waves to change one or more characteristics of the envelope-modulated electrical and magnetic fields in the target regions.

3. The system of claim 2, wherein:
the one or more parameters that change the characteristics of the envelope-modulated electrical and magnetic fields include frequency, phase, and amplitude; and
the one or more characteristics of the envelope-modulated electrical and magnetic fields include frequency, amplitude, and modulation depth.

4. The system of claim 1, wherein:
the EM wave generator comprises a phased array configured to generate multiple EM waves; and
the control circuitry is configured to control one or more parameters of the multiple EM waves such that the multiple EM waves undergo constructive and destructive interference that focuses and/or steers the multiple EM waves to the target regions.

5. The system of claim 1, wherein an amplitude of the envelope modulated electric field exceeds a threshold for neural activation.

6. The system of claim 1, wherein an amplitude of the envelope modulated electric field is below a threshold for activation of neurons within the target region.

7. The system of claim 1, wherein a minimum volume in which neurons are activated by the neuromodulation device without activating neurons outside the volume is less than about 125 cm³.

8. The system of claim 1, wherein a maximum amplitude of the envelope modulated electric field falls within the target region.

9. The system of claim 1, further comprising communications circuitry configured to transfer patient information from an additional device to the neuromodulation device; and
wherein the control circuitry is configured to modify one or more parameters of at least one of the first and second EM waves based on the patient information.

10. The system of claim 9, wherein the patient information comprises sensed physiological signals.

11. The system of claim 9, wherein the patient information are based on patient-provided input.

12. The system of claim 1, further comprising a receiver configured to receive EM waves modulated by a neural activity signal generated by neural activity within the target region.

13. The system of claim 12, wherein the control circuitry is configured to:
extract the neural activity signal from the EM waves modulated by the neural activity signal; and
control the one or more parameters of the EM waves based on the neural activity signal.

14. A method, comprising:
generating electromagnetic (EM) waves at a location remote from a patient, frequencies of the EM waves falling outside a range of frequencies that activate neurons;
directing the EM waves to one or more target region within the patient; and
intersecting the EM waves in the target regions, in each target region, intersection of the EM waves creating envelope-modulated electrical and magnetic fields having frequencies falling within the range of frequencies that activate neurons.
wherein the frequencies of the EM waves are greater than about 150 kHz and frequencies of the envelope-modulated electric and magnetic fields are less than about 100 kHz.

15. The method of claim 14, further comprising controlling one or more parameters of the first and second EM waves to change one or more characteristics of the envelope-modulated electrical and magnetic fields in the target regions.

16. The method of claim 14, further comprising receiving EM waves modulated by a neural activity signal generated by neural activity within the target region.

17. The method of claim 16, further comprising modifying parameters of the first and second EM waves based on the EM wave modulated by neural activity signal.

18. The method of claim 14, further comprising modifying parameters of the first and second EM waves based on patient information transferred from an additional device.

19. The method of claim 18, wherein the additional device is a physiological sensor implanted within or attached to the patient.

20. The method of claim 18, wherein:
the additional device includes a user interface that allows the patient to input the patient information; and
modifying the parameters comprises modifying the parameters based on information input by the patient.

* * * * *